(12) United States Patent
Chen (10) Patent No.: US 7,621,888 B2
(45) Date of Patent: Nov. 24, 2009

(54) SAFETY HYPODERMIC SYRINGE

(76) Inventor: Chang-Tzu Chen, 2F, No. 205, Sec 5, Mingshen E. Rd., Taipei (TW)

( * ) Notice: Subject to any disclaimer, the term of this patent is extended or adjusted under 35 U.S.C. 154(b) by 0 days.

(21) Appl. No.: 11/363,041

(22) Filed: Feb. 28, 2006

(65) Prior Publication Data

US 2007/0135764 A1 Jun. 14, 2007

(30) Foreign Application Priority Data

Dec. 9, 2005 (TW) .............................. 94221468 U (51) Int. Cl.
*A61M 5/00* (2006.01)
(52) U.S. Cl. ...................................... 604/110; 604/195
(58) Field of Classification Search ......... 604/221–222, 604/110, 220, 194–195
See application file for complete search history.

(56) References Cited

U.S. PATENT DOCUMENTS

| 5,458,576 | A | * | 10/1995 | Haber et al. ................. 604/110 |
| 6,582,407 | B1 | * | 6/2003 | Lo .............................. 604/220 |
| 6,592,555 | B1 | * | 7/2003 | Wen-Pi et al. ................ 604/181 |
| 2005/0096602 | A1 | * | 5/2005 | Lin ............................. 604/221 |

* cited by examiner

*Primary Examiner*—Kevin C Sirmons
*Assistant Examiner*—Deanna K Hall
(74) *Attorney, Agent, or Firm*—Guice Patents PLLC (57) ABSTRACT

A safety hypodermic syringe is disclosed to includes a barrel, which has a spiral tear groove on the front wall around a tubular neck that holds a needle assembly and a race for enabling the front wall of the barrel to be broken and carried with the needle assembly inside the barrel by a plunger after the service of the safety hypodermic syringe, and a support ring sleeved onto the tubular neck and stopped against the front wall of the barrel between the tubular neck and the race to prevent breaking of the spiral tear groove accidentally during transportation.

7 Claims, 11 Drawing Sheets

SAFETY HYPODERMIC SYRINGE

BACKGROUND OF THE INVENTION

1. Field of the Invention

The present invention relates to a safety hypodermic syringe and more particularly, to such a safety hypodermic syringe that prevents breaking of the breakable front wall of the barrel accidentally during transportation.

2. Description of the Related Art

A hypodermic syringe is an important medical instrument adapted for use to inject or withdraw liquid medicines. In recent years, the spreading of AIDS and many other diseases that are difficult to treat causes many contamination accidents. In order to prevent contamination, safety hypodermic syringes are developed. A safety hypodermic syringe is known comprising a needle assembly, a medicine barrel, a plunger, and an outer barrel. The needle assembly is fastened to the front side of the medicine barrel. The plunger is axially movably coupled to the medicine barrel and mounted with the medicine barrel inside the outer barrel. After the service of the hypodermic syringe, the plunger is pulled backwards to carry the needle cannula or the needle assembly backwards to the inside of the medicine barrel. This design of safety hypodermic syringe is functional, however it has a complicated structure and comprised of a big number of parts, resulting in a high manufacturing cost.

Taiwan Patent Publication No. 540385, issued on Jul. 1, 2003, discloses a safety hypodermic syringe entitled "Two Piece Type Retractable Safety Hypodermic Syringe". According to this design, the safety hypodermic syringe comprises a barrel, a plunger inserted into the barrel, a needle holder provided at the front side of the barrel to hold a needle, and a block with a through hole installed in the needle holder. The barrel has a tear groove on the front wall around the needle holder. After engagement of the head of the plunger with the needle holder, the plunger is pulled backwards to break the tear groove, causing the needle holder and the needle to be carried with the plunger backwards to the inside of the barrel. According to this design, the thin tear groove on the front wall of the barrel may be broken accidentally during injection or transportation of the safety hypodermic syringe, thereby causing a leakage of the fluid medicine.

Further, according to conventional designs, a residual amount of the applied liquid medicine will be left in the tubular front neck of the barrel and the hub of the needle assembly after the stopper has been pushed to the front limit position and stopped at the front wall of the barrel.

Therefore, it is desirable to provide a safety hypodermic syringe that eliminates the aforesaid drawbacks.

SUMMARY OF THE INVENTION

The present invention has been accomplished under the circumstances in view. It is the main object of the present invention to provide a safety hypodermic syringe, which is self-destructive, preventing reuse of the syringe. It is another object of the present invention to provide a safety hypodermic syringe, which expels liquid medicine completely out of the syringe during the injection, preventing residual liquid medicine in the barrel. It is still another object of the present invention to provide a safety hypodermic syringe, which keeps the needle assembly firmly secured to the inside of the barrel, preventing possible contamination.

According to one embodiment of the present invention, the safety hypodermic syringe comprises safety hypodermic syringe comprises a barrel, which comprises a fluid, a front wall, a tubular neck forwardly and perpendicularly extending from the front wall and defining a fluid passage in communication with the fluid chamber, a race forwardly and perpendicularly extending from the front wall around the tubular neck, a spiral tear groove formed on the front wall 1 adjacent to the race, and annular retaining rib extending around the inside wall of the tubular neck adjacent to the front wall, a needle assembly, which comprises a hub fitted onto the tubular neck of the barrel and a needle cannula forwardly extending from the hub, a plunger, which comprises a shank, a head at the front side of the shank, a front extension rod axially forwardly extending from the head, a conical front tip, and a front neck axially connected between the front extension rod and the conical front tip, a flexible stopper, which fits the diameter of the fluid chamber of the barrel and has a longitudinal open chamber axially extending to the rear side thereof and a front center through hole forwardly extending from the longitudinal chamber to the front side thereof for the passing of the front extension rod of the plunger, and a flexible support ring, which is sleeved onto the tubular neck and stopped against the front wall of the barrel between the tubular neck and the race. When pushed the plunger forwards after the service of the safety hypodermic syringe, the spiral tear groove is broken to separate the front wall from the barrel for enabling the broken front wall and the needle assembly to be pulled with the plunger to the inside of the barrel upon a return stroke of the plunger at this time.

According to another aspect of the present invention, the barrel has an inside annular stop flange extending around the inside wall near the rear end thereof. The head of the plunger has a front flange and a rear flange for engagement with the inside annular stop flange of the barrel after a return stroke of the plunger after the service of the safety hypodermic syringe.

According to still another aspect of the present invention, the plunger further has a rear neck connected between the shank and the head for breaking to separate the shank from the head after engagement of the front flange and rear flange of the head with the inside annular stop flange of the barrel.

According to still another aspect of the present invention, the shank of said plunger is radially ribbed, having a thumb rear at a rear end thereof. The plunger has a stopper holder formed of a parachute-like front skirt and a parachute-like rear skirt around the periphery of the front extension rod for holding the stopper. The topper has an inside annular flange formed in the rear side of the longitudinal chamber and engaged in between the front skit and rear skirt of the stopper holder of the plunger.

According to still another aspect of the present invention, the plunger further comprises a thumb rest at the rear end of the shank and a protruding strip forwardly extending from the thumb rest for stopping against the finger flange at the rear end of the barrel before the service of the safety hypodermic syringe. The protruding strip has a breakable reduced rear end connected to the thumb rest.

According to still another aspect of the present invention, the front extension rod of the plunger has a sloping face adapted to guide backward movement of the broken front wall to the inside the barrel to bias the needle assembly in the fluid chamber of the barrel after a return stroke of the plunger after the service of the safety hypodermic syringe.

According to still another aspect of the present invention, the support ring is made out of an elastic material.

DETAILED DESCRIPTION OF THE PREFERRED EMBODIMENT

Referring to FIGS. 1~4, a safety hypodermic syringe in accordance with the present invention is shown comprised of a barrel 1, a needle assembly 2, a plunger 3, a stopper 4, and a support ring 5.

Figure 1A:
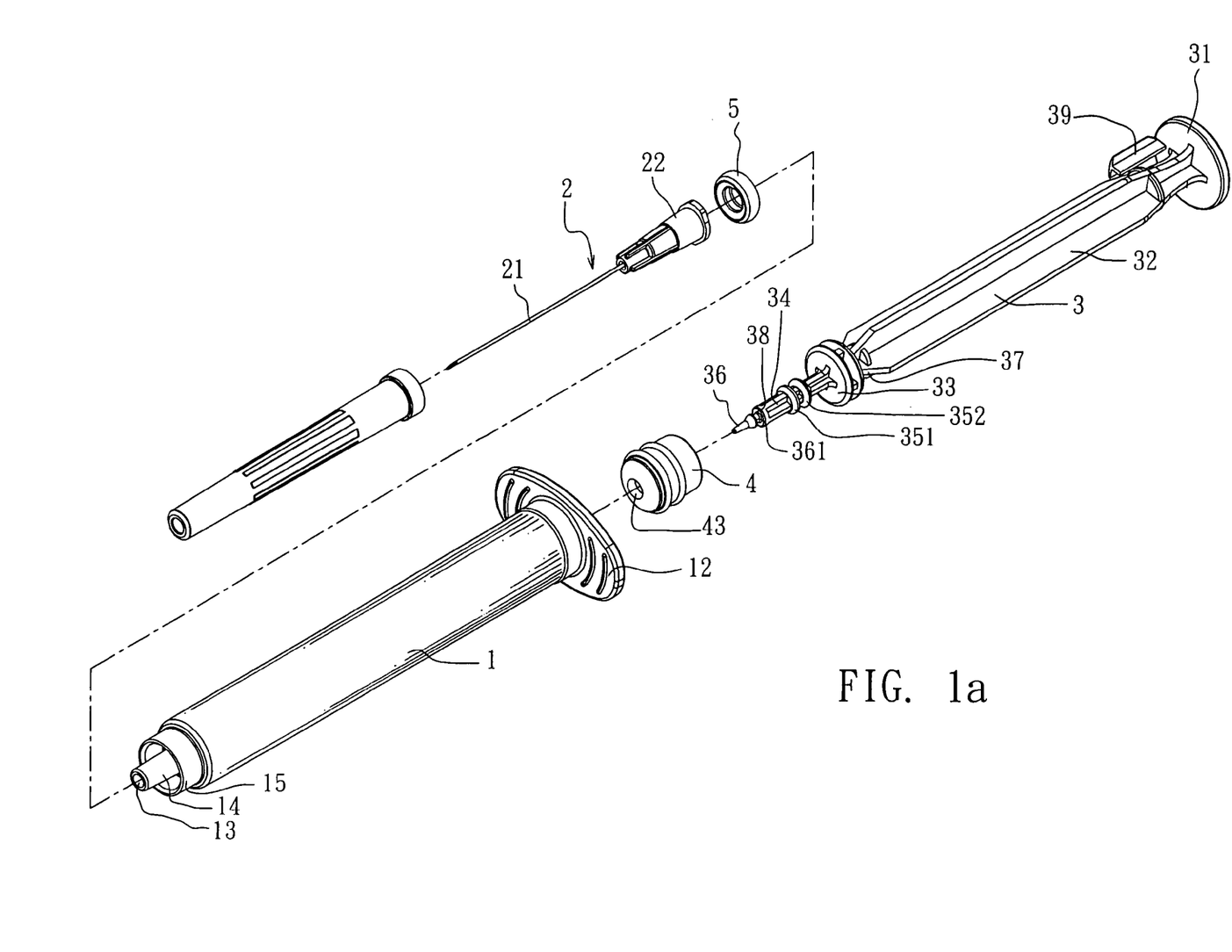
FIG. 1a is an exploded view of a safety hypodermic syringe according to a first embodiment of the present invention.
Figure 1B:
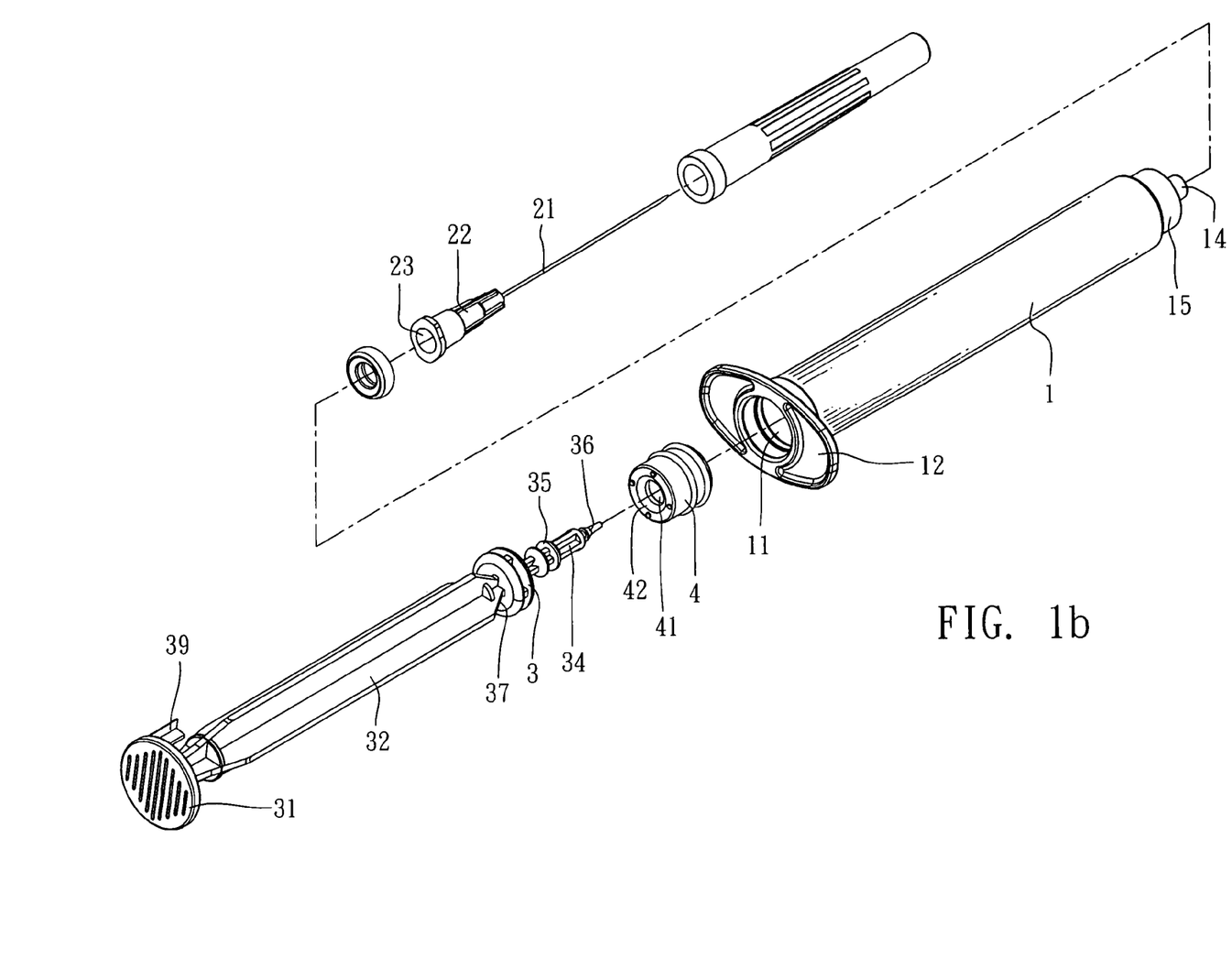
FIG. 1*b* corresponds to FIG. 1*a* when viewed from another angle.
Figure 3A:
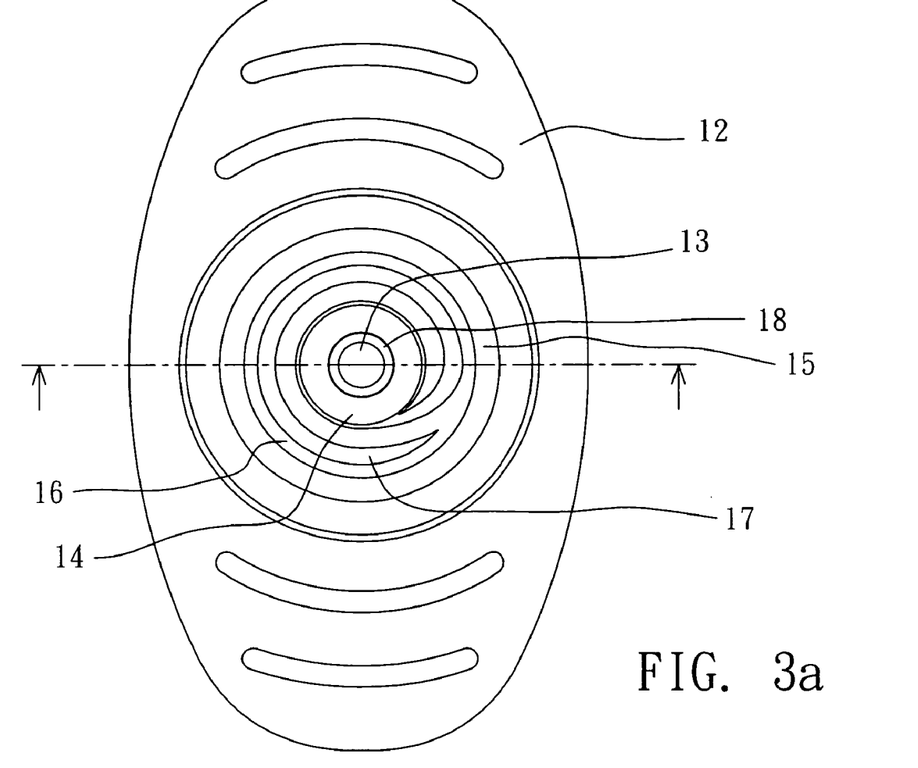
FIG. 3*a* is a top view in an enlarged scale of the safety hypodermic syringe according to the present invention.
Figure 3B:
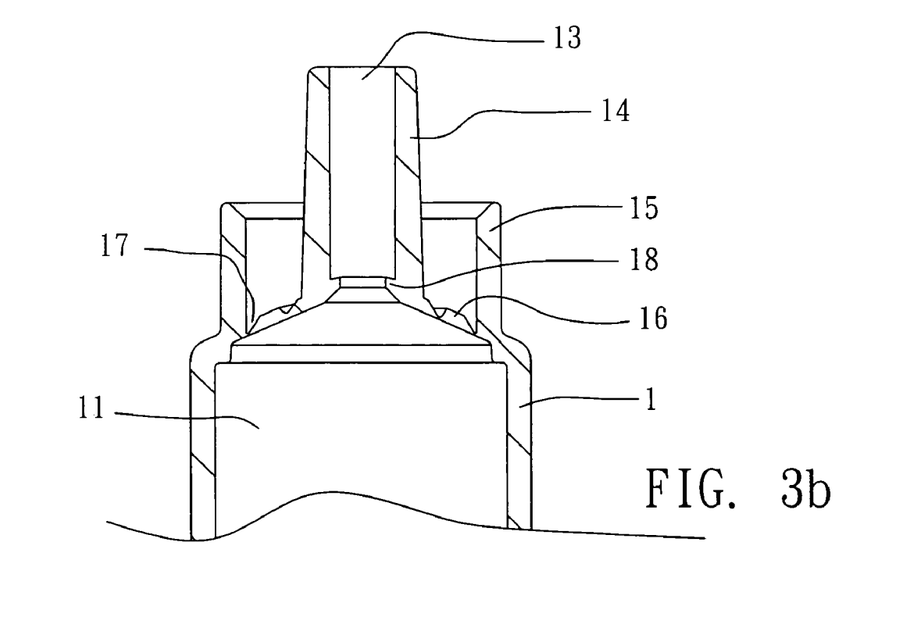
FIG. 3*b* is a sectional front view in an enlarged scale of the front part of the barrel of the safety hypodermic syringe according to the present invention.

The barrel 1 comprises a fluid chamber 11 adapted to hold a liquid medicine, a finger flange 12 extending around the periphery of the rear end thereof, a front wall 16, a tubular neck 14 forwardly and perpendicularly extending from the front wall 16 and defining a fluid passage 13 in communication between the fluid chamber 11 and the atmosphere, a race 15 forwardly and perpendicularly extending from the front wall 16 around the tubular neck 14, a spiral tear groove 17 formed on the front wall 16 adjacent to the race 15, an annular retaining rib 18 extending around the inside wall of the tubular neck 14 adjacent to the front wall 16, and an inside annular stop flange 19 extending around the inside wall corresponding to the finger flange 12.

By means of the spiral tear groove 17, the front wall 16 can easily be broken when the user pushes the plunger 3 with force, allowing the tubular neck 14 and the needle assembly 2 to be carried backwards into the inside of the barrel 1 by the plunger 3 after the service of the hypodermic syringe.

The support ring 5 is sleeved onto the tubular neck 14 and stopped against the front wall 16 of the barrel 1 between the tubular neck 14 and the race 15. The support ring 5 can be made out of a hard or flexible material. Preferably, the support ring 5 is made out of rubber. The support ring 5 has two functions. The first function of the support ring 5 is to support the front wall 16, presenting breaking of the tear groove 17 by a torque when the tubular neck 14 receives an external pressure accidentally. The second function of the support ring 5 is to prevent leakage of the contained liquid medicine out of the fluid chamber 11 when the tear groove 17 is broken accidentally.

The needle assembly 2 comprises a hub 22 and a needle cannula 21 fastened to the hub 22. The hub 22 has a mounting hole 23 fitting the periphery of the tubular neck 14 and in fluid communication with the axial center through hole of the needle cannula 21. Preferably, the tubular neck 14 and the mounting hole 23 are tapered.

The plunger 3 comprises a radially ribbed shank 32, a thumb rest 31 at the rear side of the shank 32, a head 33 at the front side of the shank 32, a front extension rod 34 axially forwardly extending from the center of the head 33, a conical front tip 36, a first neck 361 axially connected between the front end of the front extension rod 34 and the rear end of the conical front tip 36, a stopper holder 35 formed of a parachute-like front skirt 351 and a parachute-like rear skirt 352 around the periphery of the front extension rod 34 for holding the stopper 4, a second neck 37 axially connected between the front end of the shank 32 and the rear side of the head 33, a sloping face 38 at the front end of the front extension rod 34, and a protruding strip 39 forwardly extending from the thumb rest 31. The protruding strip 39 has the reduced rear end connected to the thumb rest 31 (see FIG. 4*b*). Therefore, the protruding strip 39 can easily be biased and separated from the thumb rest 31 with the hand. The protruding strip 39 is stopped against the finger flange 12 of the barrel, preventing engagement of the front tip 36 into the annular retaining rib 18 of the barrel 11 accidentally during transportation of the safety hypodermic syringe.

The stopper 4 is made out of a flexible material, for example, rubber. The outer diameter of the stopper 4 fits the diameter of the fluid chamber 11 of the barrel 1. The stopper 4 has a longitudinal open chamber 41 axially extending to the rear side, an inside annular flange 42 formed in the rear side of the longitudinal open chamber 41 and engaged in between the front skirt 351 and rear skirt 352 of the stopper holder 35 of the plunger 3, and a front center through hole 43 forwardly extending from the longitudinal chamber 41 to the front side at the center for the passing of the front extension rod 34 of the plunger 3.

Figure 2:
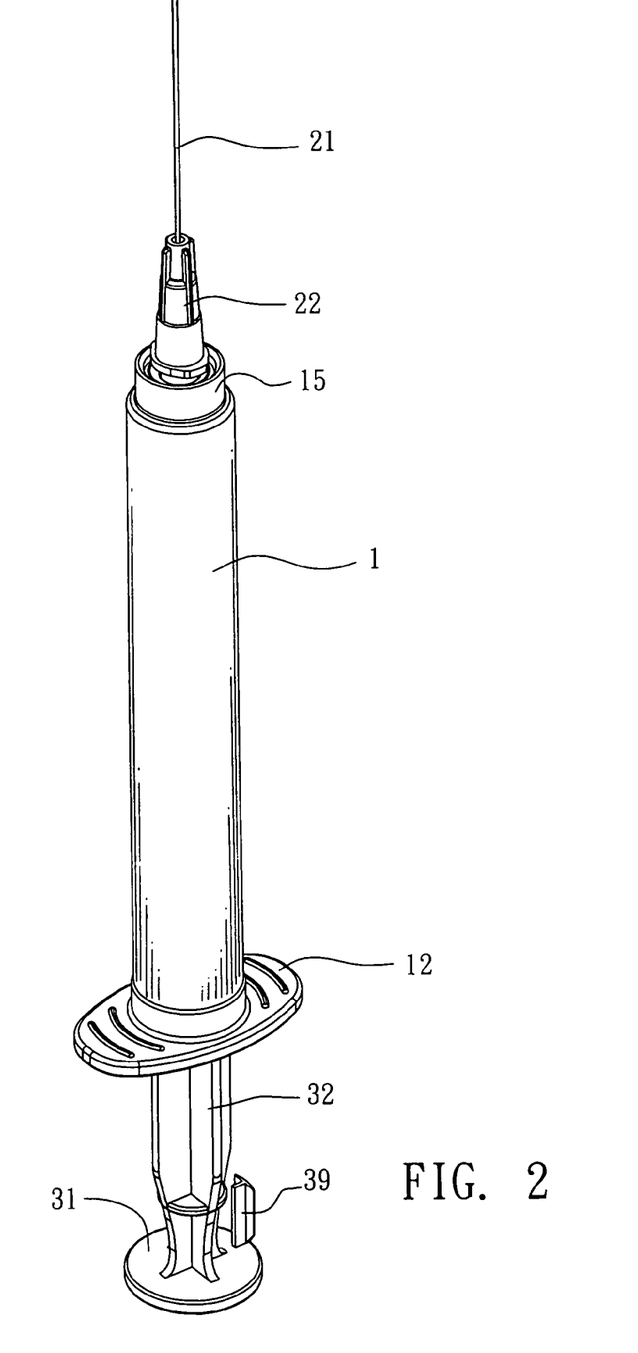
FIG. 2 is a perspective assembly view of the safety hypodermic syringe according to the present invention.
Figure 4A:
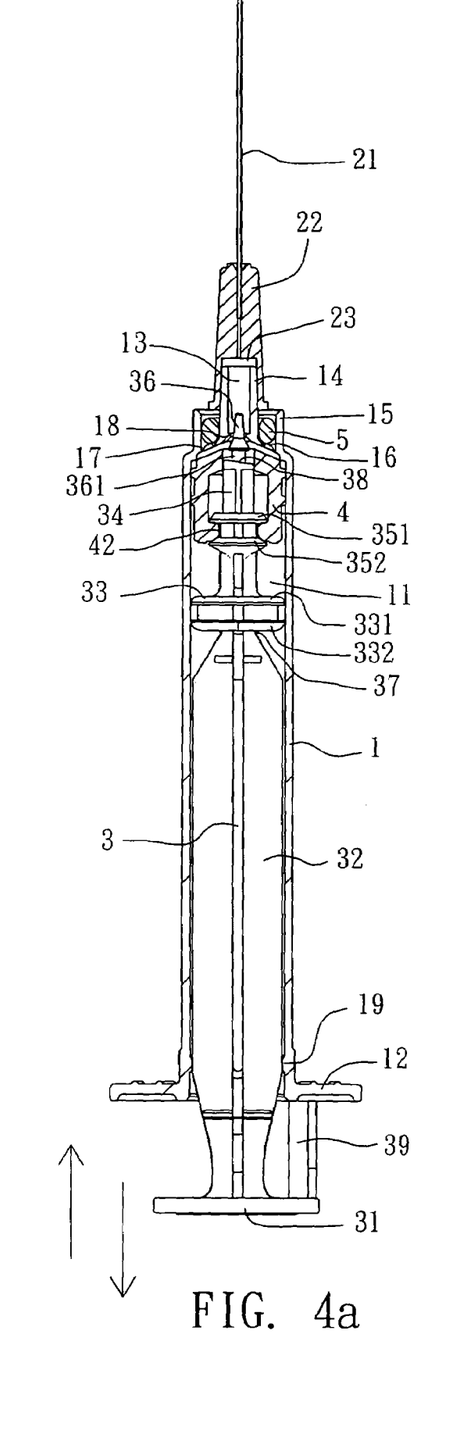
FIG. 4*a* is a sectional view of the present invention, showing a standby status of the safety hypodermic syringe.
Figure 4B:
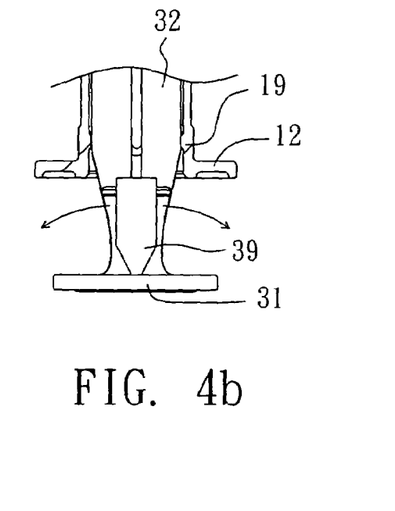
FIG. 4*b* is a schematic drawing of a part of the present invention, showing the protruding strip of the plunger biased.

During the assembly process of the present invention, the stopper 4 is fastened to the front extension rod 34 of the plunger 3 to have the conical front tip 36 extend out of the front center through hole 43 and the front skirt 351 and rear skirt 352 of the stopper holder 35 of the plunger 3 be stopped at the front and rear sides of the inside annular flange 42 of the stopper 4, and then the stopper 4 is inserted with the plunger 3 into the fluid chamber 11 of the barrel 1 from the rear side, and then the hub 21 of the needle assembly 2 is fastened to the tubular neck 14 of the barrel 1. FIG. 2 shows the assembled status of the safety hypodermic syringe. FIG. 4*a* is a sectional view of FIG. 2.

Figure 5:
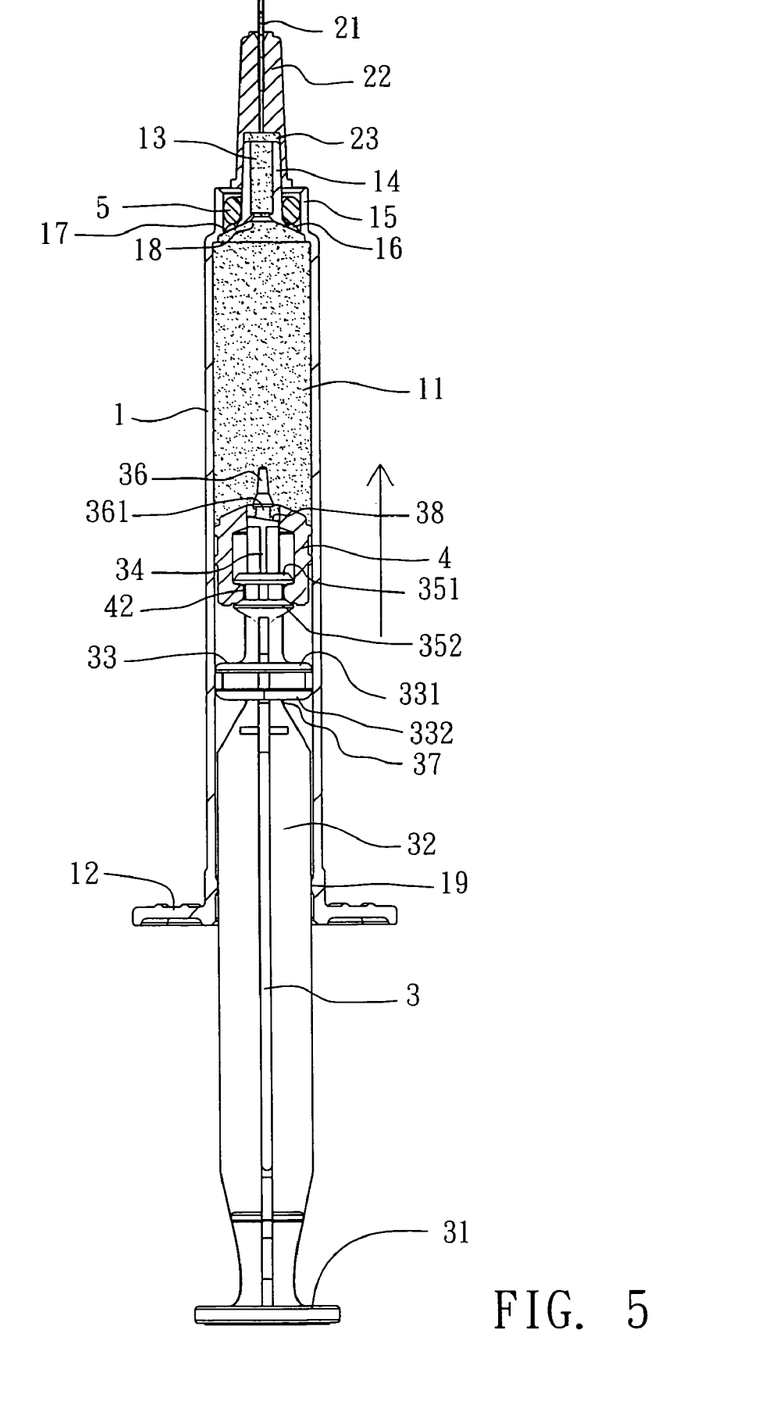
FIG. 5 is a schematic sectional view of the present invention, showing the barrel of the safety hypodermic syringe filled with a liquid medicine for injection.

After the safety hypodermic syringe has sucked in the fluid medicine for injection, as shown in FIG. 5, push the plunger 3 to move the stopper 4 forwards along the fluid chamber 11 to squeeze the fluid medicine out of the tubular neck 14 and the needle assembly 2 into the patient's body.

Figure 6:
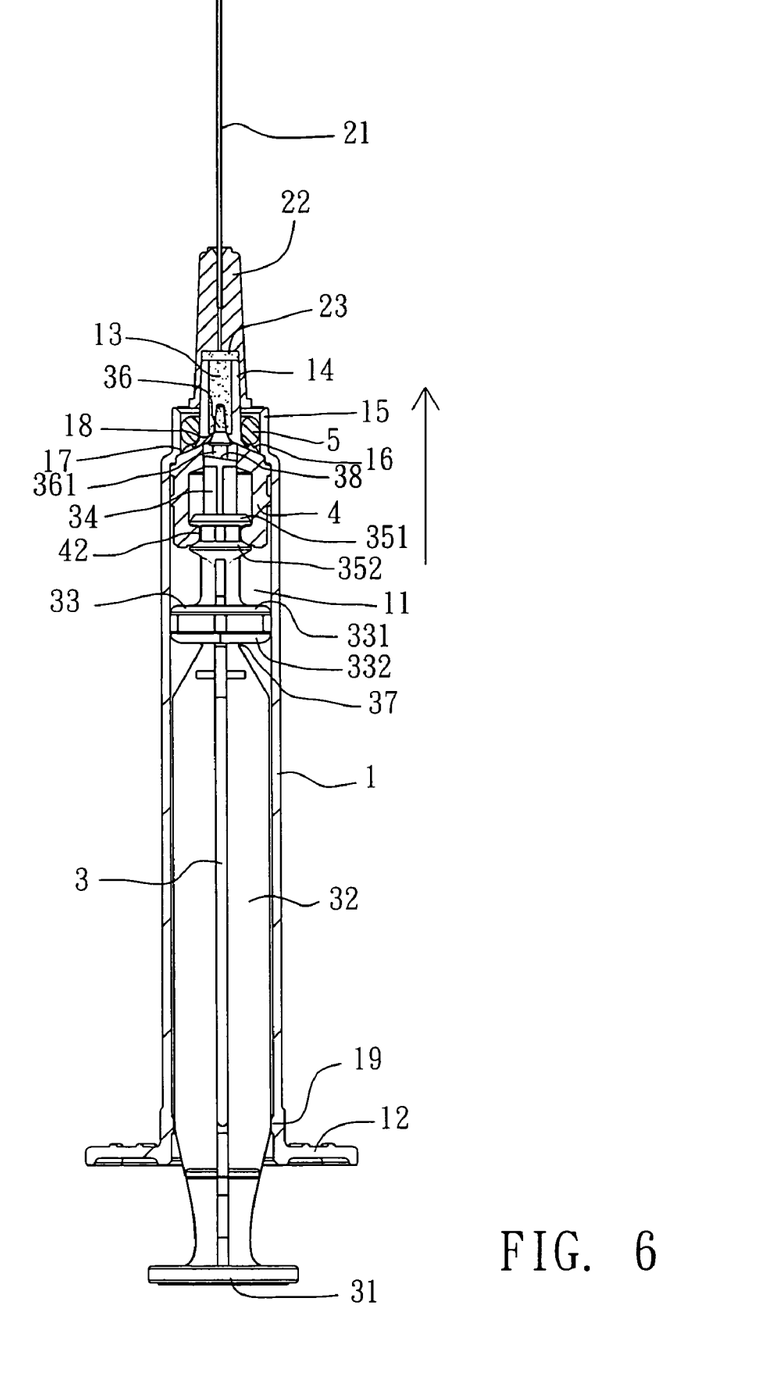
FIG. 6 is a schematic sectional view of the present invention, showing the status of the hypodermic syringe after injection.

When the stopper 4 reached the front wall 16 of the barrel 1 as shown in FIG. 6, the conical front tip 36 is forced into the fluid passage 13 of the barrel 1, preventing accumulation of residual fluid medicine in the barrel 1.

Figure 7:
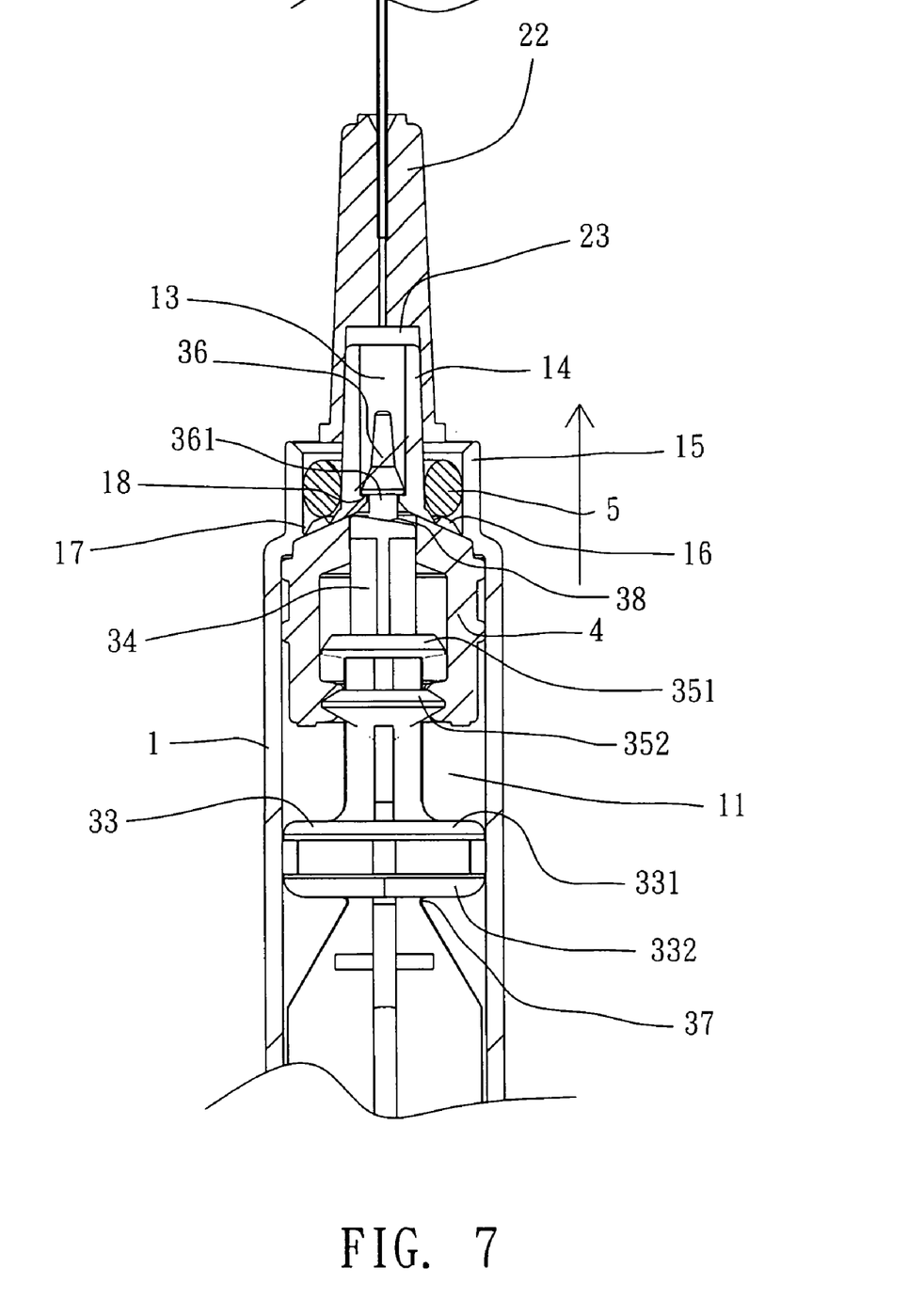
FIG. 7 is a schematic sectional enlarged view of a part of the present invention, showing the conical front tip of the plunger inserted into the fluid passage and stopped at the front side of the annular retaining rib of the barrel.
Figure 8:
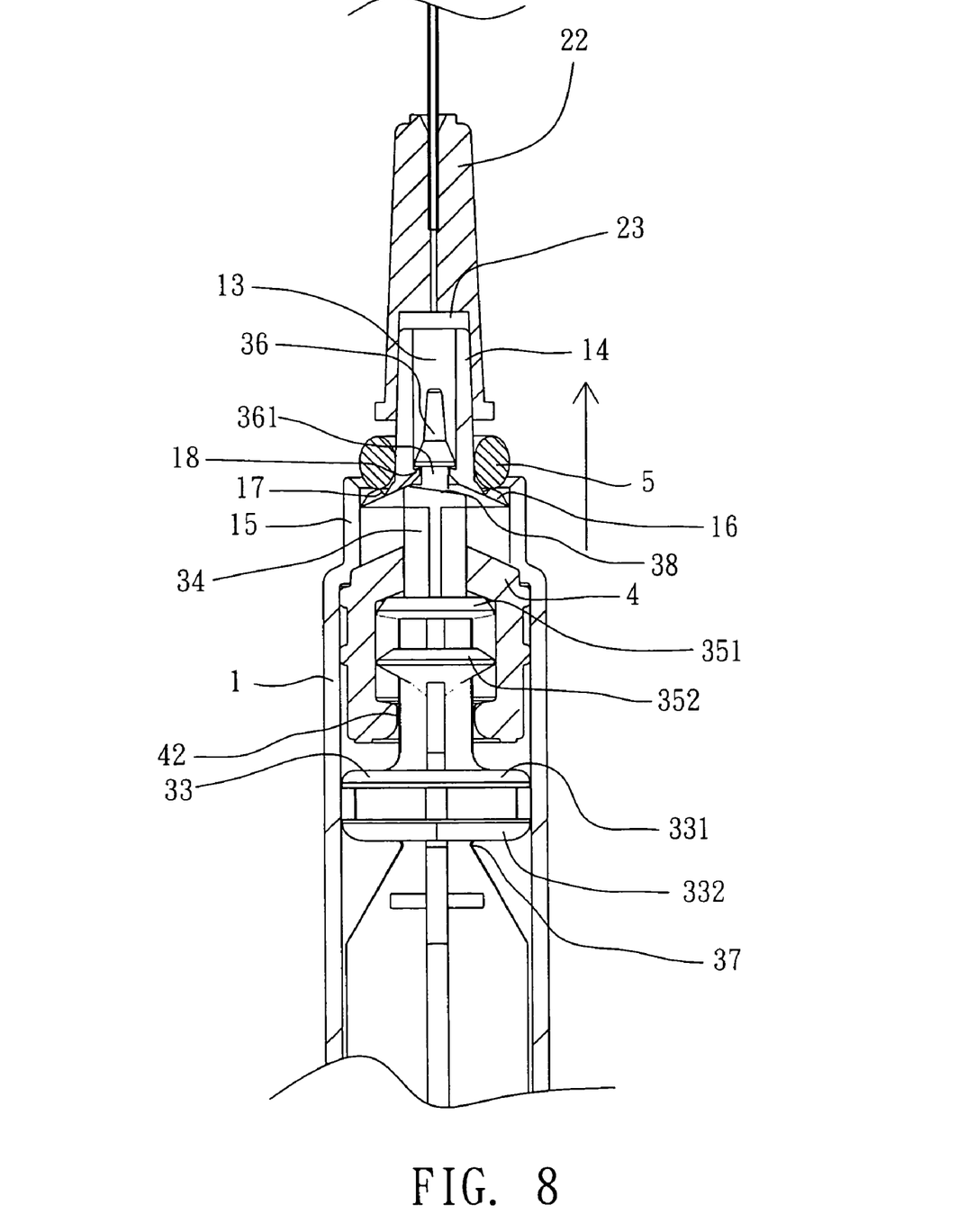
FIG. 8 is a schematic sectional enlarged view of a part of the present invention, showing the front wall of the barrel broken.

After the service of the safety hypodermic syringe as shown in FIG. 7, push the plunger 3 forwards again to force the first neck 361 into engagement with the annular retaining rib 18 inside the tubular neck 14 and simultaneously to move the front and rear skirts 351 and 352 of the stopper holder 35 into the longitudinal open chamber 41 as shown in FIG. 8. When continuously pushing the plunger 3 forwards to have the front skirt 351 be stopped against the inside annular flange 41 of the stopper 4, the spiral tear groove 17 is forced to break, causing separation of the top wall 16 from the barrel 1 At this time, the broken barrel 1 becomes useless.

Figure 9:
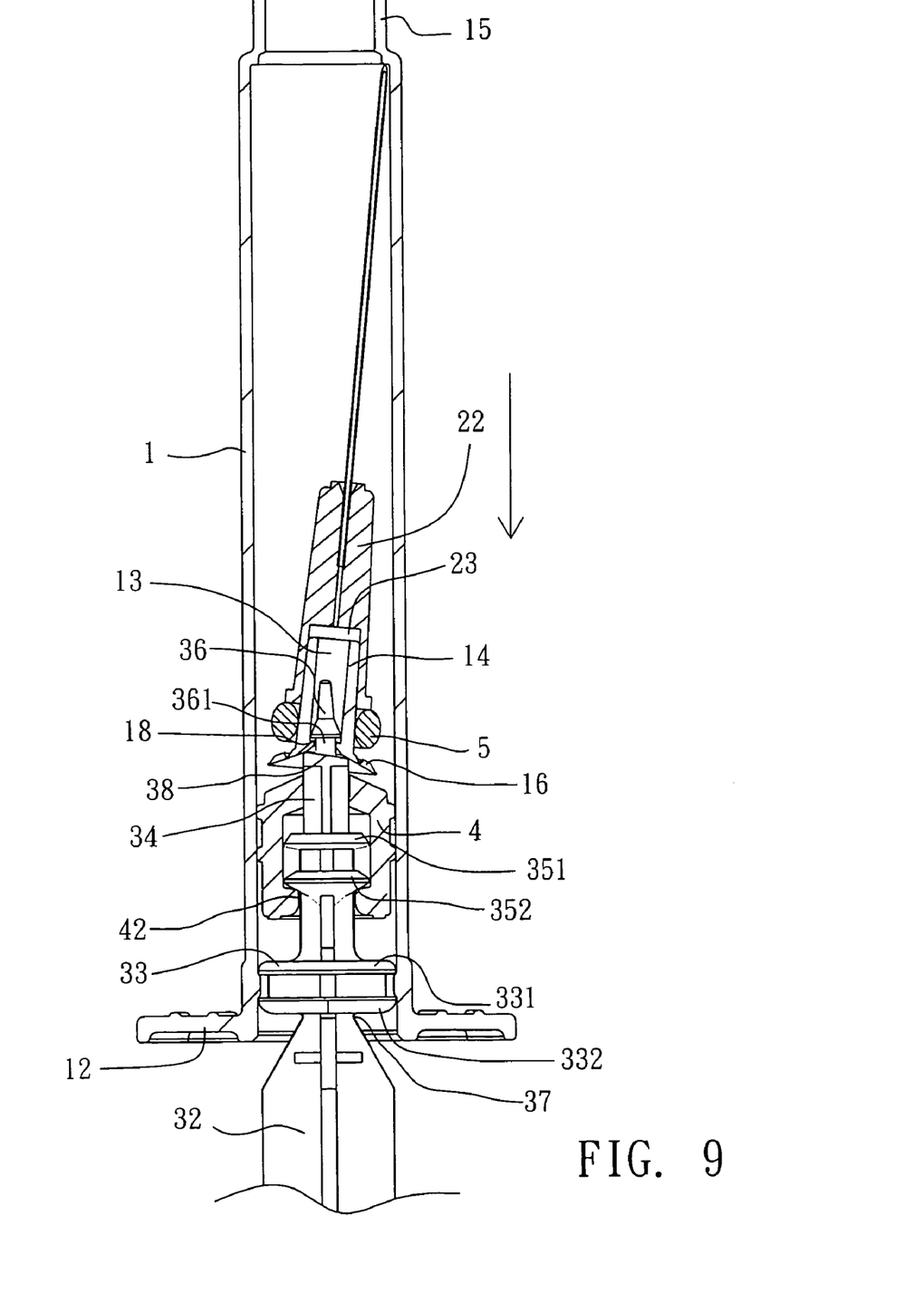
FIG. 9 is a schematic sectional enlarged view of the present invention, showing the needle assembly received inside the barrel after return stroke of the plunger.

Thereafter, the plunger 3 is pulled backwards. At this time, the stopper 4, the broken front wall 16, the support ring 5, the tubular neck 14 and the attached needle assembly 2 are carried with the plunger 3 into the inside of the fluid chamber 11 of the barrel 1 to have front flange 331 and rear flange 332 of the head 3 be respectively stopped at the front and rear sides of the inside annular stop flange 19 of the barrel 1. At this time, the broken front wall 16 is moved along the sloping face 38 of the front extension rod 36 to bias the needle assembly 2 in the fluid chamber 11 of the barrel 1.

Figure 10:
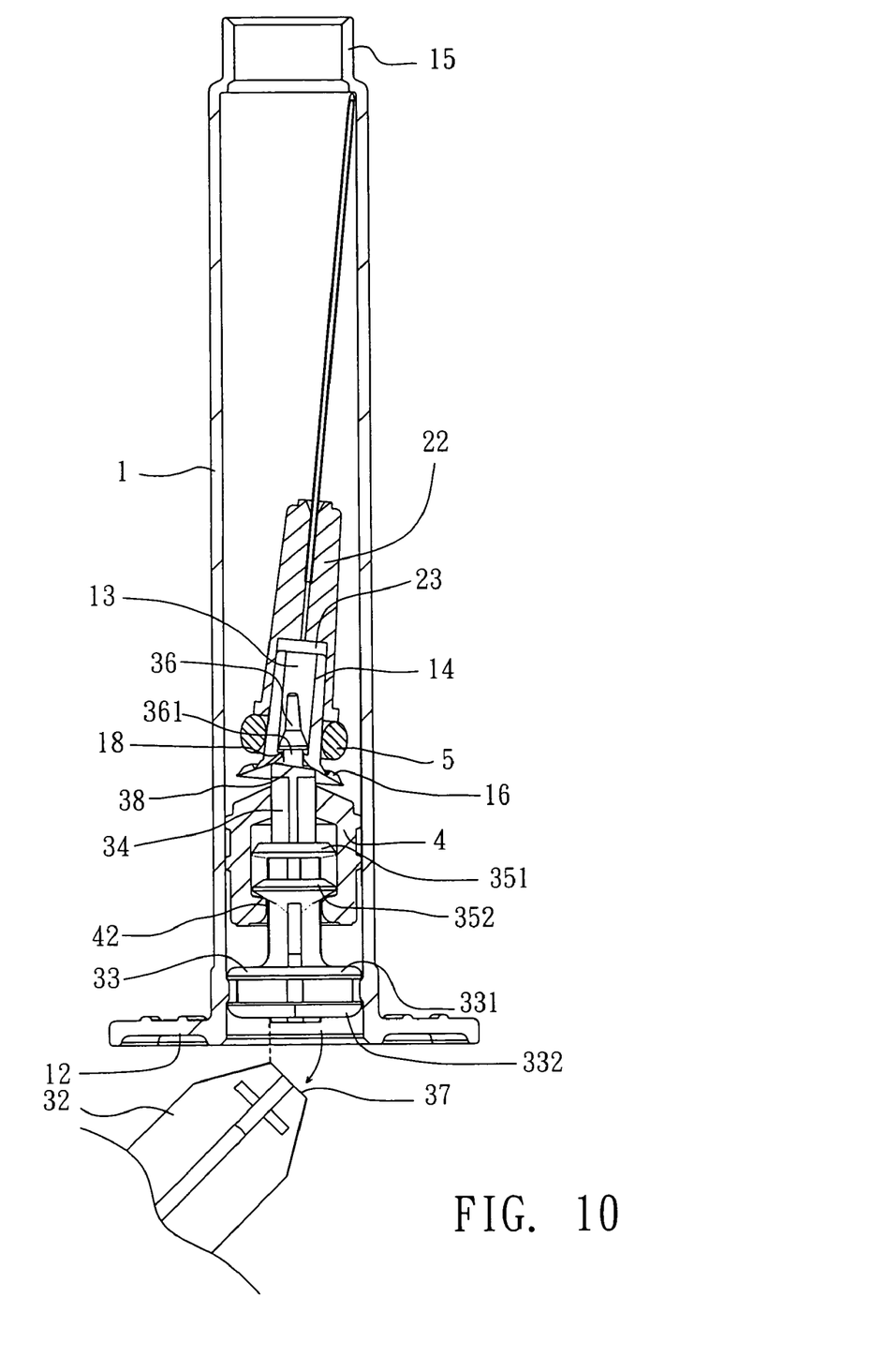
FIG. 10 is a schematic sectional enlarged view of the present invention, showing the second neck of the plunger broken, the needle assembly with the front part of the plunger left inside the barrel.

After the needle assembly 2 has been received inside the fluid chamber 11 of the barrel 1, the user can bias the shank 32 against the inside wall of the barrel 1 to break the second neck 37, as shown in FIG. 10, keeping the needle assembly 2 and a part of the plunger 3 and the stopper 4 inside the fluid chamber 11 of the barrel 1.

As indicated above, the safety hypodermic syringe enables the needle assembly to be received inside the barrel after the service, preventing a reuse of the hypodermic syringe. The support ring is sleeved onto the tubular neck and stopped against the front wall of the barrel between the tubular neck and the race to support the front wall and to prevent breaking of the tear groove accidentally and also to prevent leakage of the contained liquid medicine out of the fluid chamber when the tear groove is broken accidentally. After the service of the safety hypodermic syringe, the user can push the plunger forwards to force the first neck into engagement with the annular retaining rib inside the tubular neck and simultaneously to move the front and rear skirts of the stopper holder into the longitudinal open chamber so that continuously pushing the plunger forwards can effectively break the spiral tear groove to separate the top wall from the barrel. The design of the present invention presents excessive residual liquid medicine in the barrel. The sloping face of the front extension rod guides backward movement of the needle assembly in an oblique manner so that the needle assembly can be positively received inside the barrel after the service of the safety hypodermic syringe. Further, the foolproof design of the protruding strip at the thumb rest prevents breaking of the spiral tear groove accidentally during transportation.

A prototype of safety hypodermic syringe has been constructed with the features of FIGS. 1~10. The safety hypodermic syringe functions smoothly to provide all the features discussed earlier.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A safety syringe device comprising:
    a barrel, said barrel comprising a fluid chamber, a front wall, a race, and a tubular neck being integrally formed, said tubular neck extending forwardly and perpendicularly from said front wall, said tubular neck defining a fluid passage in communication with said fluid chamber, a race forwardly and perpendicularly extending from said front wall and being a cylindrical wall extending around said tubular neck, a spiral tear groove formed on said front wall adjacent to said race, said front wall is removably connected to adjoining ends of said race and said fluid chamber by said spiral tear groove, and an annular retaining rib extending around an inside wall of said tubular neck adjacent to said front wall;
    a needle assembly, said needle assembly comprising a hub fitted onto said tubular neck of said barrel and a needle cannula forwardly extending from said hub;
    a plunger, said plunger comprising a head at a front side of a shank thereof, a front extension rod axially forwardly extending from said head, a conical front tip, and a first neck axially connected between said front extension rod and said conical front tip;
    a flexible stopper fitting the diameter of said fluid chamber of said barrel, said stopper having a longitudinal open chamber axially extending to a rear side thereof and a front center through hole forwardly extending from said longitudinal open chamber to a front side thereof for the passing of the front extension rod of said plunger; and
    a flexible support ring sleeved onto said tubular neck and stopped against an exterior surface of said front wall of said barrel and located between said tubular neck and said race of said barrel and located between said race of said barrel and said front wall of said barrel;
    wherein when pushed said plunger moves forward after the service of the syringe device, said spiral tear groove is broken to separate said front wall from said barrel enabling the broken front wall and said needle assembly to be pulled with said plunger to an interior of said barrel upon a return stroke of said plunger at this time,
    wherein the spiral tear groove begins at a central point and coils increasingly outwards from the central point,
    wherein said flexible support ring is located between said spiral tear groove and said race and said flexible support ring preventing said spiral tear groove from breaking due to a movement of said needle assembly when said needle assembly is sleeved onto said tubular neck,
    wherein said plunger has a stopper holder located between said head and said conical front tip of said plunger and having a parachute-like front skirt and a parachute-like rear skirt spaced apart and located around an exterior periphery of said front extension rod for holding said stopper, said parachute-like front skirt is located between said first neck and said parachute-like rear skirt; said stopper has an inside annular flange formed in the rear side of said longitudinal open chamber opposite said front center through hole;
    wherein said parachute-like front skirt and said parachute-like rear skirt are moveable between a first position and a second position relative to said plunger, when said parachute-like front skirt and said parachute-like rear skirt are located in the first position, said inside annular flange of said stopper is located between said parachute-like front skirt and said parachute-like rear skirt of said stopper holder of said plunger and said front center through hole of said stopper is located between said parachute-like front skirt and said first neck of said plunger,
    wherein when said parachute-like front skirt and said parachute-like rear skirt are located in the second position, parachute-like front skirt and said parachute-like rear skirt of said stopper holder of said plunger are located between said inside annular flange of said stopper and said front center through hole of said stopper.

2. The safety syringe device as claimed in claim 1, wherein said barrel has an inside annular stop flange extending around an inside wall near a rear end thereof; said head of said plunger has a front flange and a rear flange for engagement with the inside annular stop flange of said barrel after a return stroke of said plunger after the service of the safety syringe device.

3. The safety syringe device as claimed in claim 1, wherein said plunger further has a rear neck connected between said shank and said head for breaking to separate said shank from said head after engagement of the front flange and rear flange of said head with the inside annular stop flange of said barrel.

4. The safety syringe device as claimed in claim 1, wherein said support ring is made out of an elastic material.

5. The safety syringe device as claimed in claim 1, wherein said shank of said plunger is radially ribbed, having a thumb rest at a rear end thereof.

6. The safety syringe device as claimed in claim 1, wherein said front extension rod of said plunger has a sloping face adapted to guide backward movement of said broken front wall to the inside said barrel to bias said needle assembly in said fluid chamber of said barrel after a return stroke of said plunger after the service of the safety syringe device.

7. The safety syringe device as claimed in claim 1, wherein said plunger further comprises a thumb rest at a rear end of said shank and a protruding strip forwardly extending from said thumb rest for stopping against a finger flange at a rear end of said barrel before the service of the safety syringe device, said protruding strip having a breakable reduced rear end connected to said thumb rest.

\* \* \* \* \*